United States Patent [19]

Sheldon et al.

[11] 4,179,917
[45] Dec. 25, 1979

[54] LOW PRESSURE DEW AND FROST POINT INDICATOR

[75] Inventors: Robert S. Sheldon; Jan W. Rabek, both of Northridge, Calif.

[73] Assignee: Air-Dry Corporation of America, Northridge, Calif.

[21] Appl. No.: 861,267

[22] Filed: Dec. 16, 1977

[51] Int. Cl.² .................................................. G01N 25/68
[52] U.S. Cl. .................................................... 73/17 A
[58] Field of Search ................................... 73/17 A, 23

[56] References Cited
U.S. PATENT DOCUMENTS

| | | | |
|---|---|---|---|
| 2,624,195 | 1/1953 | Van Alen | 73/17 |
| 2,680,371 | 6/1954 | Donath | 73/17 |
| 2,769,339 | 11/1956 | Brailsford | 73/17 |
| 3,152,475 | 10/1964 | Ford et al. | 62/5 |
| 3,281,814 | 10/1966 | Roth | 73/17 |
| 3,460,373 | 8/1969 | Ford | 73/17 |
| 3,874,220 | 4/1975 | Sheldon | 73/17 |
| 3,886,784 | 6/1975 | Sheldon | 73/17 |

OTHER PUBLICATIONS

"The Lectrodryer Dew point Apparatus" in McGraw-Edison Bulletin LAB-A1 SM271.
General Eastern Corporation, 1200 Series Dew Point Hygrometer Specifications.
E.G.G. Model 444, Dew Point Hygrometer Bulletin, 3-140.

Primary Examiner—Herbert Goldstein
Attorney, Agent, or Firm—Lyon & Lyon

[57] ABSTRACT

A low pressure dew and frost point indicator of the type having a vortex tube which directs a cold air stream against the back of a viewing mirror for observation of the initial formation of frost. The mirror has means for simple and automatic centering with respect to the cold air stream of the vortex tube for maximum temperature transfer. The mirror engages no heat conducting elements and has means for improved cold temperature transfer. A venturi nozzle passes the warm air output of the vortex tube around the cold air output for adjustment to provide optimum cold air generation by reduction of the vortex tube outlet pressure. A temperature control valve controls the temperature in the sample chamber by mixing the warm and cold air outputs of the vortex tube.

41 Claims, 3 Drawing Figures

LOW PRESSURE DEW AND FROST POINT INDICATOR

BACKGROUND OF THE INVENTION

1. Field of the Invention

The invention relates to a low pressure dew and frost point indicator and more particularly to the cooling module of such an indicator.

2. Description of the Prior Art

The prior art known to the applicants is best represented by the prior Sheldon U.S. Pat. Nos. 3,874,220 and 3,886,784, Ford U.S. Pat. Nos. 3,374,658, 3,152,475 and 3,460,373 and Hankison U.S. Pat. No. 3,589,165.

In prior devices, there has been no positive and simple way of positioning the frost point indicating mirror correctly with respect to the cold air stream which is directed against it.

Prior mirrors have also been subject to temperature gradients and undesirable changes of temperature caused by contact with adjacent module components and/or subjection to atmospheric or high pressure gases entering from the surrounding area.

Ejectors of the type used in the prior art have not had the capability of being adjusted for optimum operation of the cold air generation system and then being pre-set in optimum setting.

In case a new reading is required, necessitating raising the temperature in the sampling chamber, the prior art has utilized purge or blow down valves to clear the sample chamber or has cut off air controlled by the input to the sample chamber with relatively large valves in order to allow the sample chamber to become warmer.

SUMMARY OF THE INVENTION

The present invention provides a low pressure dew and frost point indicator and more particularly a cooling module for such an indicator which is an improvement over devices of the type now in use.

It is an object of the invention to provide a device of the type described in which the viewing mirror can be easily and precisely oriented with respect to the source of cold air which impinges against it.

Another object is to provide a viewing mirror which has improved cold air transfer means, which is substantially thick in order to avoid temperature gradients and which is mounted in such a manner as to be insulated from temperature changes caused by contact with adjacent metallic components and/or adjacent atmospheric or high pressure gases.

A further object of the invention is to provide a contrast mirror formed of identical material and having a polished surface substantially identical with that of the viewing mirror. The contrast mirror is also protected from temperature changes caused by its environment.

Another object of the invention is to provide means for lighting the sample chamber for better observation of the mirrors, which utilizes the transfer of light through plastic components disposed adjacent to the sample chamber.

A still further object of the invention is to provide an ejector which is an integral part of the cooling module, which can be adjusted and pre-set for optimum generation of cold air by the vortex tube, and which utilizes novel means of causing warm air to flow around the outside of cold air to create the desired venturi effect for pressure reduction at the outlet.

It is another object of the invention to provide a novel control valve for use in raising the temperature of the sample chamber. A small needle valve having minimal fluid flow is utilized as a "spoiler" to mix the hot and cold air in order to warm the sample chamber.

It is also among the objects of the invention to provide a low pressure dew and frost point indicator and cooling module therefor having all of the advantages and benefits of the structure described above and set forth in greater detail hereinafter in this specification.

The invention also comprises such other objects, advantages and capabilities as will later more fully appear and which are inherently possessed by the invention.

DESCRIPTION OF THE PREFERRED EMBODIMENT

Figure 1:
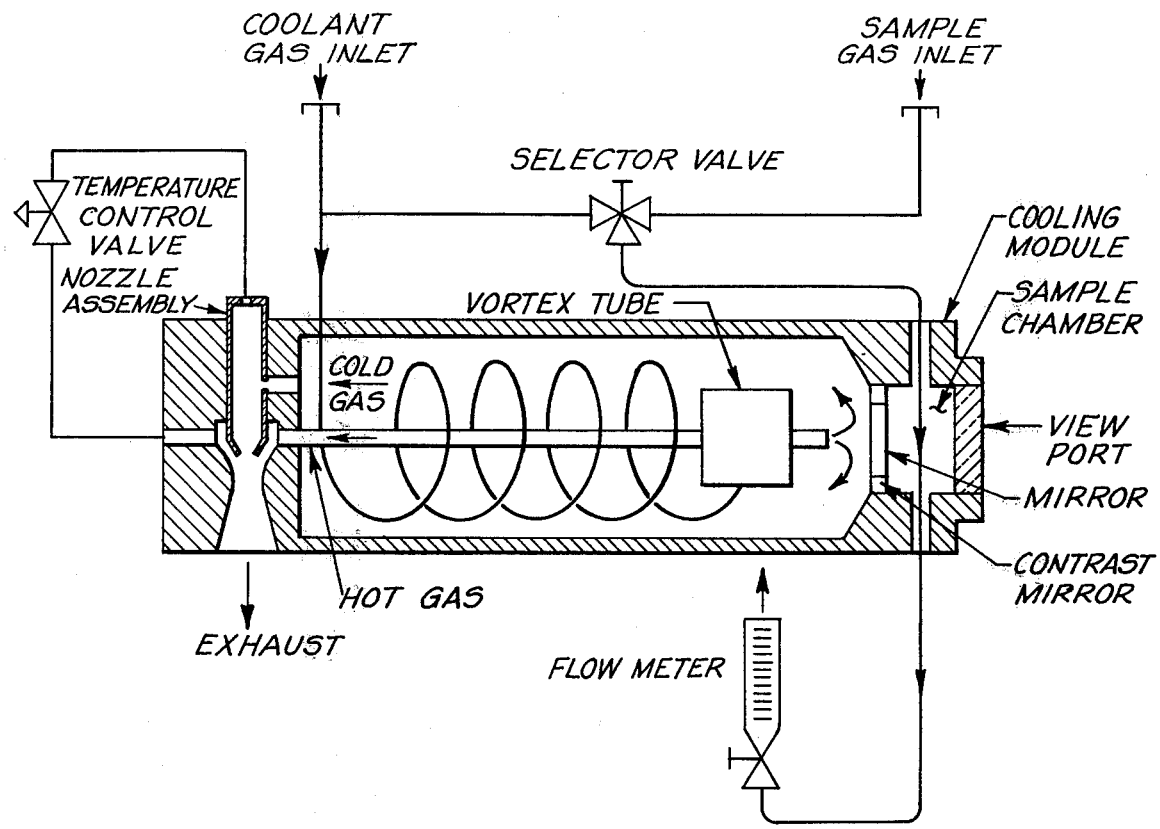
FIG. 1 is a schematic flow diagram of the cooling module and related components of the dew and frost point indicator.

A preferred embodiment which has been selected to illustrate the invention is shown in schematic form in FIG. 1 of the drawings. A selector valve controls the flow of coolant gas or sample gas to and through the sample chamber of a cooling module. A viewing mirror, which is surrounded by a contrast mirror, is observed through a view port to note when condensation occurs on the viewing mirror. A flow meter measures the flow through the sample chamber.

Cold gas under pressure is supplied to a vortex tube, which divides it into a cold fraction and a hot fraction. The cold fraction is impinged against the back of the viewing mirror. The hot fraction flows in the opposite direction toward the exhaust.

A venturi structure which will be described more fully, acts to reduce the outlet pressure of the vortex tube in order to improve its cold air generation ability. A temperature control valve, which will also be described more fully, acts to control the temperature within the sample chamber.

Figure 2:
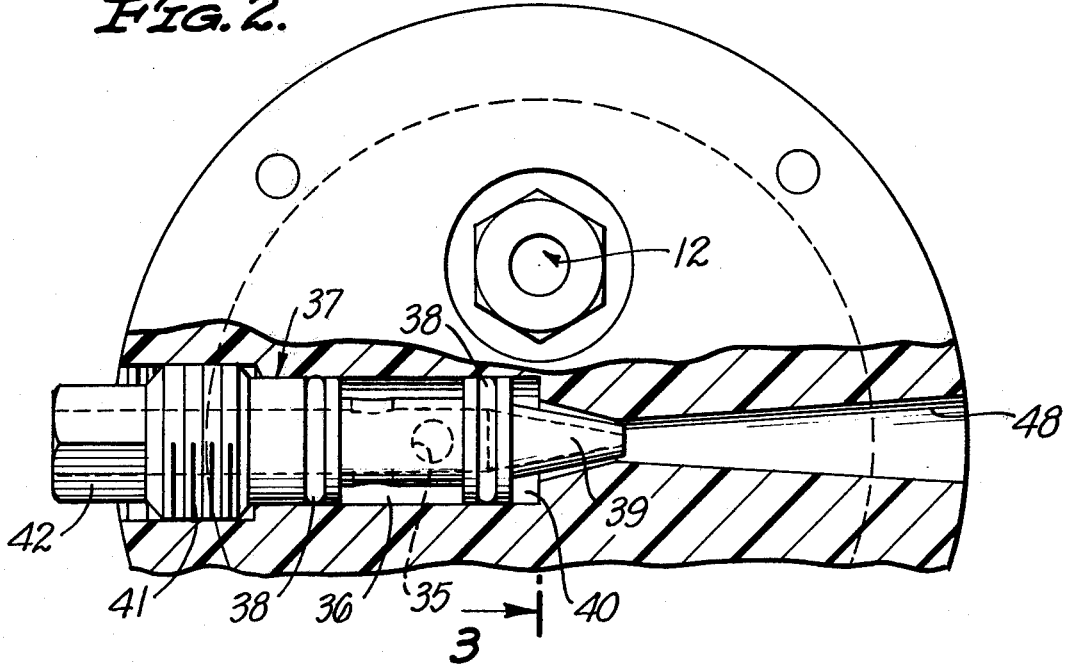
FIG. 2 is an end view of the cooling module, partially broken away to show the interior structure.
Figure 3:
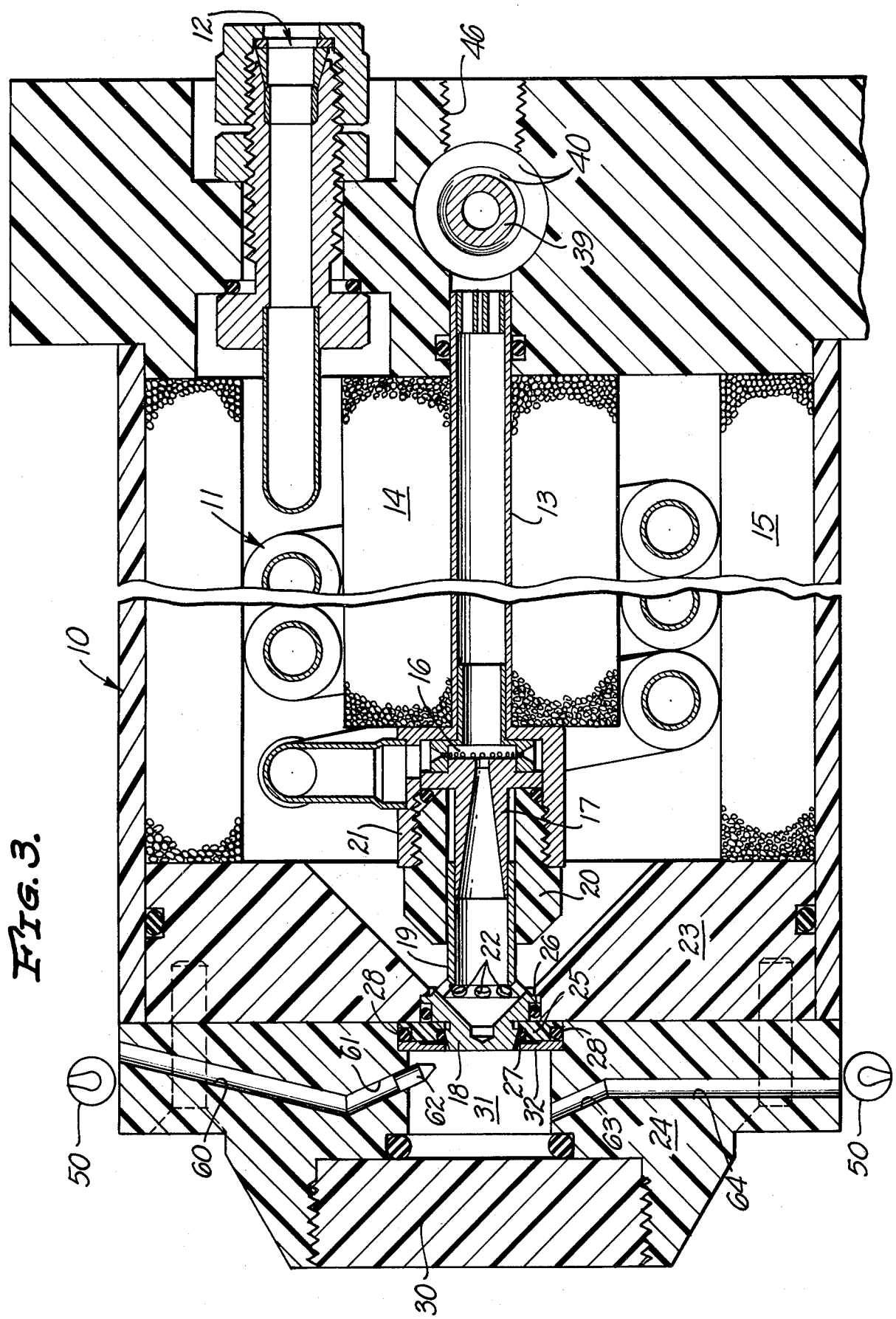
FIG. 3 is a longitudinal sectional view of the cooling module, taken on line 3—3 of FIG. 2.

The cooling module is shown in detail in FIGS. 2 and 3 of the drawings. Referring to FIG. 3, the cooling module comprises a housing 10 which encloses a conventional vortex tube 11 of the Ranque-Hilsch type. It is an instrument which is capable of converting a supply of compressed air or gas into hot and cold fractions. The module includes inlet means 12 for supplying the coolant air or gas to the vortex tube 11. An outlet tube 13, which carries the warm air component of the vortex tube toward the exhaust outlet, is surrounded by an inner insulator 14. An outer insulator 15 extends around the outside of the helical linings of the vortex tube 11.

The vortex tube 11 injects air or gas at sonic speed circumferentially into a vortex generating chamber 16, from which heated air is driven through the outlet tube 13 in one direction and cold air is driven in the opposite direction through a cold air outlet 17 having a circular exterior and a funnel-shaped interior.

A viewing mirror 18 is preferably formed of copper. It has an integral tubular portion 19 which is constructed and arranged to fit slidably over the outer portion of the cold air outlet 17 of the vortex tube 11. The outside of the tubular portion 19 of the viewing mirror 18 is held by the interior of a plastic adapter screw 20. The adapter screw 20 is threadedly connected with the pre-cooling assembly 21 of the vortex tube 11, which surrounds the generating chamber 16.

The viewing mirror 18 is accordingly easily oriented and securely held in its proper position with respect to the cold air outlet 17 by its integral tubular portion 19 being held between the cold air outlet 17 and the adapter screw 20.

Precise centering of the viewing mirror with respect to the cold air stream directed against it is necessary in order to achieve the full potential of the cold air stream. If the cold air is not properly directed, a substantial amount of cooling effect can be lost.

It will be noted from FIG. 3 that the opposite end of the viewing mirror 18, which comprises the back of its viewing surface, is comparatively thick. This provides a better transfer of temperature from the cold air stream to the mirror 18. It also acts to minimize or eliminate temperature gradients across the surface of the mirror.

The mirror 18 is provided with a plurality of angularly directed air outlets 22, through which air flows outwardly after it has impinged against the back of the mirror 18. The mirror 18 is preferably formed from a solid piece of copper, in which the outlets 22 are drilled first in the form of openings having circular cross sections. The interior of the mirror 18 is then drilled axially, intersecting the previously drilled outlets 22. The interior of the mirror 18 is thereby left with a plurality of integral thin webs or fins which surround the outlets 22 within the interior of the mirror 18. These webs or fins assist in the transfer of cold temperature from the cold air stream to the mirror 18.

The mirror 18 is held in place entirely by plastic components, which are good insulators and which do not undesirably affect the mirror temperature as would metallic components. These plastic elements include a mirror housing 23, a mirror head 24 which is secured by fasteners to the mirror housing 23 and a mirror sealing plate 25, all of which are preferably formed of Plexiglas or other suitable comparable material.

Three O-rings 26, 27 and 28 act to keep atmospheric pressure, vacuum and high pressure air from reaching the mirror 18. This prevents any change in the temperature of the mirror 18 caused by contact with adjacent air or gas.

It should be noted that the mirror 18 contacts only the plastic components, which are effective temperature insulators, and the O-rings, which are also temperature insulators.

A viewing lens 30 is mounted in the front of the mirror head 24. The sample chamber 31 is disposed between the viewing lens 30 and the face of the mirror 18. A contrast mirror 32, which is also made of copper, is mounted in surrounding relationship to the viewing mirror 18. The inner edge of the contrast mirror 32 is spaced slightly from the outer periphery of the viewing mirror 18. Only the outer edge of the contrast mirror 32 is held between the O-ring 28 and a step formed in the mirror head 24. The inner portion of the back of the contrast mirror 32 is cut away to space it from contact with the mirror sealing plate 25.

Since the viewing mirror 18 and the contrast mirror 32 are formed of the same material, their viewing surfaces which are observed through the viewing lens 30 are preferably polished to present an identical appearance. This makes it easier for the observer to determine the point of initial condensation on the surface of the viewing mirror 18 by observing its change in appearance with respect to the contrast mirror 32.

The cold air which flows out of the mirror 18 through the outlet openings 22 flows concentrically around the coils of the vortex tube 13 in order to provide pre-cooling of the air or gas before it enters the generating chamber 16.

When the cold air reaches the exhaust unit of the vortex tube 11, it flows through one or more passages 35 into a chamber 36 formed in the midportion of a nozzle assembly 37. (FIG. 2) A pair of O-rings 38 are disposed on opposite sides of the chamber 36. From the chamber 36, the cold air flows outwardly through the interior of a tapered outlet nozzle 39.

At the same time, the warm air flows through the outlet tube 13 into an outer chamber 40 which extends around the outside of the nozzle 39. The chamber 40 has a portion which tapers slightly more than the exterior of the nozzle 39 to form a narrow passage surrounding the outlet of the nozzle 39.

This structure provides a venturi action in which the warm air from the outlet tube 13 creates a partial vacuum around the outlet of the cold air nozzle 39. This results in evacuating the cold air from the vortex tube 11 at sub-atmospheric pressure. It is known that the temperature drop through the vortex tube 11 is related to the absolute pressure ratio between the inlet and the cold air outlet of the vortex tube. If a small vacuum is pulled from the cold air outlet, the temperature drop of the vortex tube 11 is increased. It is accordingly possible to generate colder air for impingement against the back of the mirror 18.

It should be noted that in the present device the warm air is disposed around the outside of the nozzle 39, while the cold air passes through the interior of the nozzle 39. This is opposite from structures of a similar type found in the prior art. It is simpler and more efficient and produces better results.

From the nozzle 39 and chamber 40 both the cold and warm air are ejected through an outwardly flared port 48 which extends through the side of the interior end of the housing 10.

The nozzle assembly 37 includes a passage which extends in the opposite direction from the chamber 36 through a threaded portion 41 and out through a hexagonal adjusting nut 42. The nut 42 can be rotated to adjust the position of the nozzle assembly 37 with respect to the end of the housing 10. This adjusts the position of the nozzle 39 with respect to the surrounding chamber 40 in order to adjust the width of the passage adjacent to the end of the nozzle 39. The position of the nozzle assembly 37 is preferably adjusted only one time for optimum generation of cold air by the vortex tube 11 and is then kept in the desired optimum setting.

The adjustable nozzle assembly 37 acts as a metering or needle valve which increases the efficiency of the vortex tube and optimizes the entire operation of the instrument. With this structure, it is feasible to incorporate the ejector or venturi member into the cooling module rather than to provide a separate unit as in the prior art.

If it becomes necessary to warm the air in the sample chamber 31, this can be done by opening the temperature control valve which is shown on the left side of FIG. 1 of the drawings. This valve is connected to the open end of the passage which extends through the nut 42. This passage is in turn connected to the cold air chamber 36 in the nozzle assembly 37. The temperature control valve is also connected to a warm air discharge opening 46 which is formed in the end of the housing 10. When the temperature control valve is opened, the warm and cold air are mixed together and the cold air generation of the vortex tube 11 is partially or completely destroyed. This operation is similar in effect to an electrical short circuit.

The temperature control valve comprises a small valve which has little flow, as opposed to large valves which were required in prior devices to shut off the input coolant gas to the vortex tube in order to achieve the same purpose. The temperature control valve is small enough to be mounted on the front panel of the instrument to provide remote pneumatic control of the temperature in the assembly chamber.

Since the accuracy of the instrument is dependent upon observation of the initial formation of frost on the viewing mirror 18, means may be provided to improve the lighting of the sample chamber 31 in which the face of the viewing mirror 18 is disposed. Such means comprises a pair of light bulbs 50, which are indicated schematically in FIG. 3 of the drawings. The light bulbs 50 are preferably located along opposite sides of the mirror head 24. Since the plastic from which the mirror head 24 is formed has excellent light conductive properties, light from the bulbs 50 travels transversely through the mirror head 24 into the sample chamber 31 to provide better lighting for observation of the mirror 18. The bulbs 50 may also serve as an on-off indicator for the instrument as well.

The sample stream enters the sample chamber 31 from passages 60 and 61. Passage 61 is angled in such a manner as to direct its outlet toward the center of the viewing mirror 18. A nozzle 62 may be utilized in the end of the passage 61 to further concentrate the flow. After striking the viewing mirror 18, the sample stream flows out through the passages 63 and 64.

Instead of the light means shown in FIG. 3 of the drawings, we may install a source of collimated light which extends diagonally through the mirror head 24 to project collimated light directed toward the center of the viewing mirror 18.

We claim:

1. In a low pressure dew and frost point indicator of the type in which a vortex tube directs a cold air stream against the back of a viewing mirror for observation of the initial formation of frost on the surface of the viewing mirror, the improvement comprising:
   (a) means for centering and holding said viewing mirror in a fixed position with respect to said cold air output for maximum transmission of temperature change from said cold air stream to said mirror, said means comprising a tubular member extending rearwardly from said viewing mirror and fitting over the cold air output of said vortex tube, said tubular member being elongated and being formed integrally with said viewing mirror; and
   (b) a plastic adapter member extending around said cold air stream outlet, said tubular member of said viewing mirror being held between said adapter member and said cold stream output.

2. The structure described in claim 1, said mirror being held free from engagement with any temperature conductive members.

3. The structure described in claim 2, said viewing mirror engaging only plastic elements and O-rings which are substantially non-conductive of temperature changes.

4. The structure described in claim 1 including a plurality of angularly directed outlet holes through the wall of the tubular member for outward flow of cold air after the cold air has impinged on the back of the mirror.

5. The structure of claim 4 wherein the interior wall of the tubular member includes irregularities in the form of fins at least partially around said outlet holes, said fins assisting in the cooling of the mirror by the cold air stream.

6. The structure described in claim 1, the portion of said mirror extending rearwardly from the face thereof being substantially thick for improved transmission of temperature change and to prevent gradients across the face of said mirror.

7. The structure of claim 1 wherein said viewing mirror engages only plastic elements and O-rings which are substantially nonconductive of temperature changes.

8. The structure described in claim 1, and a contrast mirror concentrically surrounding said viewing mirror, said contrast mirror being formed from the same material as said viewing mirror and having a substantially identical polished viewing surface, said contrast mirror being held without substantial engagement with any heat-conductive elements.

9. The structure described in claim 1, and means for applying light to the face of said mirror to improve the accuracy of observation of the formation of frost on said mirror.

10. The structure of claim 9 in which the means for applying light comprises a source of collimated light.

11. In a low pressure dew and frost point indicator of the type in which a vortex tube directs a cold air stream against the back of a viewing mirror for observation of the initial formation of frost on the surface of the mirror, the improvement comprising means for adjustably controlling and maximizing the cold air generation in said vortex tube, said means comprising a nozzle assembly including a tapered nozzle connected to the cold air output of said vortex tube, a tapered chamber surrounding said nozzle and connected to the warm air output of said vortex tube, said nozzle assembly being adapted to reduce the cold air output pressure of said vortex tube to thereby improve the cold air generation of said vortex tube, means for longitudinally adjusting the position of said nozzle with respect to said surrounding opening for optimum generation of cold air by said vortex tube and means for setting said nozzle in said position.

12. The structure described in claim 11, said vortex tube and mirror being mounted in a cooling module housing, said nozzle assembly being threadedly mounted in the end of said housing remote from said mirror, said adjusting means being operable from outside said housing.

13. The structure set forth in claim 11, and means for temporarily reducing the cold air generation of said vortex tube without changing the setting of said nozzle by mixing the cold and warm air outputs of said vortex tube.

14. The structure described in claim 13, in which said warm and cold air outlets are taken from the end of said housing in which said needle assembly is mounted.

15. The structure set forth in claim 14, in which said indicator has a front panel and said means comprises a needle valve mounted on said front panel and operable remotely from said needle assembly.

16. The structure described in claim 11, and means for applying light to the face of said mirror to improve the accuracy of observation of the formation of frost on said mirror.

17. The structure of claim 16 in with the means for applying light comprises a source of collimated light.

18. In a method for determining the moisture content of a sample gas in which a collant gas is introduced to a vortex tube which discharges a cold gas and a warm gas and the cold gas is directed against a viewing mirror for observation of condensation of moisture of the sample gas on the mirror, the improvement comprising evacuating the cold gas by passing spent cold gas through a tapered outlet nozzle and passing warm gas through a chamber extending around the nozzle, wherein the chamber tapers more than the nozzle for forming a narrow passage surrounding the outlet of the nozzle, thereby generating a venturi effect for reducing the pressure of the cold gas discharged by the vortex tube relative to the introduction pressure of the coolant gas to the vortex tube, thereby increasing the temperature drop through the vortex tube.

19. The method of claim 18 wherein the sample gas and the coolant gas are the same.

20. The method of claim 18 including the step of passing through the tapered outlet nozzle;
(e) a chamber extending around the outlet nozzle, and means for passing warm gas through the chamber wherein the chamber tapers more than the outlet nozzle to form a narrow passage surrounding the outlet of the nozzle, thereby providing a venturi effect for reducing the pressure of the cold gas discharged by the vortex tube to subatmospheric pressure; and
(f) means for adjusting the pressure of the cold gas discharged by the vortex tube for adjusting the temperature drop through the vortex tube.

21. The method of claim 20 in which the spent cold gas is passed around the vortex tube countercurrent to the flow of gas in the vortex tube.

22. The method of claim 18 including the step of adjusting the size of the passage for adjusting the temperature drop across the vortex tube.

23. The method of claim 18 including the step of passing warm gas from the chamber into the nozzle for at least partially short circuiting the venturi effect for adjusting the temperature drop through the vortex tube.

24. The method of claim 18 including the additional step of varying the pressure of the cold gas discharged by the vortex tube for varying the temperature drop in the vortex tube.

25. The method of claim 18 in which the pressure of the cold gas discharged by the vortex tube is reduced to subatmospheric pressure.

26. The method of claim 18 including the step of passing warm gas into the nozzle.

27. A method for determining the moisture content of a sample gas comprising the steps of:
(a) introducing a coolant gas into a vortex tube which discharges a cold gas and a warm gas;
(b) directing the cold gas against a viewing mirror for observation on the mirror of condensation from a sample gas;
(c) passing spent cold gas which has been directed against the mirror through a tapered outlet nozzle and passing warm gas through a chamber extending around the outlet nozzle, wherein the chamber tapers more than the outlet nozzle to form a narrow passage surrounding the outlet of the nozzle, thereby reducing the pressure of the cold gas discharged by the vortex tube to sub-atmospheric pressure; and
(d) adjusting the pressure of the cold gas discharged by the vortex tube for adjusting the temperature drop through the vortex tube.

28. The method of claim 27 in which the step of adjusting the pressure of the cold gas discharged from the vortex tube comprises the step of passing a selected amount of warm gas from the chamber into the nozzle.

29. In a moisture indicator comprising means for introducing a coolant gas into a vortex tube which discharges a cold gas and a warm gas and directs the cold gas against a viewing mirror for observation of condensation on the mirror of moisture of the sample gas, the improvement comprising means for evacuating the cold gas dicharged by the vortex tube relative to the introduction pressure of the coolant gas to the vortex tube, thereby increasing the temperature drop through the vortex tube, the means for evacuating the cold gas comprising a tapered outlet nozzle, means for passing spent cold gas through the nozzle, a chamber extending around the nozzle and means for passing warm gas through the chamber, wherein the chamber tapers more than the nozzle forming a narrow passage surrounding the outlet of the nozzle, through which the warm gas passes, thereby generating a venturi effect.

30. The indicator of claim 29 wherein the sample gas and the coolant gas are the same.

31. The indicator of claim 29 including a tubular member extending rearwardly from the mirror and fitting over the cold air output of the vortex tube and outlet holes through the wall of the tubular member for passing spent cold gas which has been directed against the mirror around the vortex tube.

32. The indicator of claim 29 including means for passing spent cold gas that has been directed against the mirror around the vortex tube to cool the gas in the vortex tube.

33. The indicator of claim 32 in which the spent cold gas is passed around the vortex tube countercurrent to the flow of gas in the vortex tube.

34. The indicator of claim 29 including means for adjusting the size of the passage for adjusting the temperature drop across the vortex tube.

35. The indicator of claim 29 including a pathway between the chamber and the nozzle for passing warm gas from the chamber into the nozzle for at least partially short circuiting the venturi effect for adjusting the temperature drop through the vortex tube.

36. The indicator of claim 35 including valve means in the pathway for adjusting the amount of warm air passing through the pathway for varying the temperature drop through the vortex tube.

37. The indicator of claim 29 including means for varying the pressure of the cold gas discharged by the vortex tube for varying the temperature drop in the vortex tube.

38. The indicator of claim 29 in which the means for evacuating reduces the pressure of the cold gas discharged by the vortex tube to sub-atmospheric pressure.

39. The indicator of claim 29 including means for passing warm gas into the nozzle.

40. A device for determining the moisture content of a sample gas comprising:
 (a) a vortex tube;
 (b) means for introducing a coolant gas into the vortex tube which discharges a cold gas and a warm gas;
 (c) means for directing the cold gas discharged by the vortex tube against a viewing mirror for observation of condensation from the sample gas on the mirror;
 (d) a tapered outlet nozzle and means for passing spent cold gas which has been directed against the mirror through the tapered outlet nozzle;
 (e) a chamber extending around the outlet nozzle, and means for passing warm gas through the chamber wherein the chamber tapers more than the outlet nozzle to form a narrow passage surrounding the outlet of the nozzle, thereby providing a venturi effect for reducing the pressure of the cold gas discharged by the vortex tube to subatmospheric pressure; and
 (f) means for adjusting the pressure of the cold gas discharged by the vortex tube for adjusting the temperature drop through the vortex tube.

41. The device of claim 40 in which the means for adjusting the pressure of the cold gas dicharged from the vortex comprises a pathway for passing warm gas form the chamber into the nozzle and valve means in the pathway for adjusting the amount of warm gas passed from the chamber into the nozzle.

* * * * *